(12) United States Patent
Meyer-Boehm et al.

(10) Patent No.: US 8,846,085 B2
(45) Date of Patent: Sep. 30, 2014

(54) METHOD FOR PRODUCTION OF DIRECTLY COMPRESSIBLE IBUPROFEN FORMULATIONS

(75) Inventors: Kathrin Meyer-Boehm, Feucht (DE); Karl Kolter, Limburgerhof (DE); Anisul Quadir, Hackettstown, NJ (US)

(73) Assignee: BASF SE (DE)

( * ) Notice: Subject to any disclaimer, the term of this patent is extended or adjusted under 35 U.S.C. 154(b) by 859 days.

(21) Appl. No.: 12/089,416

(22) PCT Filed: Oct. 5, 2006

(86) PCT No.: PCT/EP2006/067058
§ 371 (c)(1),
(2), (4) Date: Apr. 7, 2008

(87) PCT Pub. No.: WO2007/042445
PCT Pub. Date: Apr. 19, 2007

(65) Prior Publication Data
US 2008/0213361 A1 Sep. 4, 2008

(30) Foreign Application Priority Data
Oct. 11, 2005 (DE) .......................... 10 2005 049 001

(51) Int. Cl.
*A61K 9/20* (2006.01)
*A61K 9/22* (2006.01)
*A61K 9/26* (2006.01)
*C07C 63/04* (2006.01)
*A61K 31/19* (2006.01)
*A61K 31/192* (2006.01)

(52) U.S. Cl.
CPC .............. *A61K 31/192* (2013.01); *A61K 9/2095* (2013.01); *A61K 9/2009* (2013.01); *A61K 9/2054* (2013.01)
USPC ........... 424/470; 424/464; 424/465; 424/468; 424/469; 562/493; 514/570

(58) Field of Classification Search
None
See application file for complete search history.

(56) References Cited

U.S. PATENT DOCUMENTS

| | | | |
|---|---|---|---|
| 5,191,114 A * | 3/1993 | Chen | 562/496 |
| 6,951,657 B1 | 10/2005 | Zuccarcelli et al. | |
| 2006/0062847 A1* | 3/2006 | Kolter et al. | 424/464 |
| 2006/0240102 A1* | 10/2006 | Kolter et al. | 424/464 |

FOREIGN PATENT DOCUMENTS

| | | | |
|---|---|---|---|
| EP | 0172014 B1 | 2/1986 | |
| EP | 0 172 014 B1 * | 1/1991 | ............ A61K 31/19 |
| JP | 62-294637 | 12/1987 | |
| WO | WO-92/08686 A1 | 5/1992 | |
| WO | WO-94/10993 A1 | 5/1994 | |
| WO | WO-2005/037192 A2 | 4/2005 | |

OTHER PUBLICATIONS

Roberts et al.; J. of Pharmacy and Pharmacology; vol. 56, Iss. 3, pp. 299-305 (2004).*

* cited by examiner

*Primary Examiner* — Jeffrey T Palenik
(74) *Attorney, Agent, or Firm* — Drinker Biddle & Reath LLP

(57) ABSTRACT

A directly tabletable ibuprofen formulation comprising a) 50-99% by weight of crystalline ibuprofen, b) 1-15% by weight of a finely divided excipient with a surface area of at least 100 m²/g, and c) 0-40% by weight of further excipients, with the proviso that the total amount of components a) to c) corresponds to 100% by weight, where at least 50% of the surface of the ibuprofen crystals are covered with the finely divided excipient.

31 Claims, No Drawings

METHOD FOR PRODUCTION OF DIRECTLY COMPRESSIBLE IBUPROFEN FORMULATIONS

RELATED APPLICATIONS

This application is a national stage application (under 35 U.S.C. 371) of PCT/EP2006/067058, filed Oct. 5, 2006, which claims benefit of German application 10 2005 049 001.8, filed Oct. 11, 2005.

BACKGROUND OF THE INVENTION

The present invention relates to an improved process for producing directly tabletable ibuprofen formulations by mixing ibuprofen with a finely divided excipient, and to the formulations obtained correspondingly.

Direct tableting is a process frequently used in the production of tablets because it is simpler and more cost-efficient. Direct tableting is therefore becoming increasingly important.

Up to 800 mg of ibuprofen is administered per tablet. Since it is wished to ensure that there are no swallowing problems, the ibuprofen content in ibuprofen tablets is normally very high. This high ibuprofen content in an ibuprofen formulation leads to the properties for example of the tableting mixture being determined almost exclusively by the properties of ibuprofen. The low melting point of ibuprofen of only 75° C. therefore causes serious difficulties in the processing of a formulation, such as, inter alia, adhesion to the compression tools and low tableting speeds. Besides the tendency to adhere, the high ibuprofen content also frequently leads to poor flowability because the ibuprofen crystals are usually in a form with a size in the region of 50 µm.

The unwanted phenomenon of adhesion to the compression tools increases as the duration of a production cycle increases. On the other hand, a manufacturer will always attempt, for cost reasons, to have a production cycle running for as many hours as possible without, for example, polishing or dismantling punch tools.

Problems arise in the processing of ibuprofen-containing mixtures especially with relatively low compressive forces too. On the other hand, a pharmaceutical manufacturer will always attempt to operate with compressive forces which are as low as possible in order to save the high-cost compression tools from wear.

In general, problems arise during processing of ibuprofen owing to its tendency to adhere because of the relatively low melting point. Even during the mixing process to produce dry ibuprofen-containing mixtures there may be sticking of the mixing tools especially with a high energy input and heating of the agitators.

U.S. Pat. No. 5,191,114 discloses a process for producing ibuprofen powders for direct tableting, in which powders with improved flowability are said to be obtained by dry mixing of ibuprofen with amorphous silica gel. As is known to the skilled worker, the flowability can be improved in this way after only a short mixing time. However, the tabletability is not improved in practice in this way.

EP-A 172 014 likewise describes the production of ibuprofen-containing formulations, where the ibuprofen is mixed with sodium croscarmellose as disintegrant and small amounts of colloidal silica with short mixing times in the region of a few minutes, and is subsequently roll-compacted. An insufficient improvement in tabletability is achieved with these formulations too.

WO 2005/037192 likewise describes the production of ibuprofen-containing granules by dry mixing of the active ingredient with pharmaceutical aids and subsequent roll compaction.

DESCRIPTION OF THE INVENTION

It was an object of the present invention to find improved ibuprofen formulations and an improved process for producing directly compressible ibuprofen.

We have found that this object is achieved by a process for producing directly compressible ibuprofen formulations by mixing ibuprofen with a finely dispersed excipient, which comprises a mixture of 50 to 99% by weight of a crystalline ibuprofen with 1 to 15% by weight of a finely divided excipient with a surface area of from 100 to 300 $m^2/g$ and 0 to 40% by weight of further excipients, where the total amount of mixing components is 100% by weight, until the surface of the ibuprofen crystals is at least 50% covered with the finely dispersed excipient.

The invention further relates to directly tabletable ibuprofen formulations which are obtained by the process of the invention.

It is possible according to the invention to employ ibuprofen in the form of the free acid or as salt, suitable salts being alkali metal or alkaline earth metal salts or salts with a basic amine or in the form of amino acid salts, for example lysinate salts. Preferred salts are the sodium and potassium salts, in particular sodium ibuprofenate. The ibuprofen is employed according to the invention in the form of crystalline particles. The average particle size of the ibuprofen particles is preferably from 20 to 200 µm, particularly preferably from 25 to 110 µm.

The process of the invention is preferably carried out in such a way that at least 60%, particularly preferably at least 70%, of the surface of the ibuprofen crystals are covered with the finely divided excipient.

The finely divided excipient can have a specific surface area or from 100 to 300 $m^2/g$ (measured by the BET method), preferably at least 150 $m^2/g$, particularly preferably at least 200 $m^2/g$, very particularly preferably at least 250 $m^2/g$. The average particle size of the primary particles of the excipient can be from 2 to 200 nm, preferably 5 to 100, particularly preferably 5 to 50, nm.

Suitable finely divided excipients are in particular metal oxides, preferably oxides selected from the group of the oxides of aluminum, silicon, zinc and of titanium. Oxides of silicon are particularly preferred, it being possible to employ besides finely divided silica also hydrophobized silicas. Hydrophobized silicas can be obtained for example by reacting the silanol groups with dichlorodimethylsilane, octylsilane or hexamethyldisilazane. Finely divided silica is very particularly preferably employed, in particular with average particle sizes of the primary particles of from 5 to 50 nm.

The ibuprofen formulations of the invention may comprise further conventional excipients such as fillers, binders, disintegrants and lubricants or mixtures thereof.

Fillers which can be employed are microcrystalline cellulose, cellulose, calcium hydrogen phosphate, mannitol, sorbitol, xylitol or lactose, preferably microcrystalline cellulose.

Binders which can be employed are polyvinylpyrrolidone, vinylpyrrolidonelvinyl acetate copolymers, hydroxypropyl methylcellulose, hydroxypropylcellulose, hydroxyethylcellulose or methylcellulose. Microcrystalline cellulose can also be employed as binder.

Suitable disintegrants are crosslinked sodium carboxymethyl starch, crosslinked sodium carboxymethylcellulose (croscarmellose sodium) or crosslinked polyvinylpyrrolidone.

Lubricants which can be employed are stearic acid, magnesium stearate, sodium stearyl fumarate, leucine, sodium benzoate or poloxamers.

The ibuprofen formulations of the invention preferably comprise
a) 50-95% by weight of ibuprofeh,
b) 1-15% by weight of finely divided silica with a surface area of at least 150 m$^2$/g,
c) 5-20% by weight of microcrystalline cellulose,
d) 0-10% by weight of crosslinked polyvinylpyrrolidone, crosslinked sodium carboxymethylcellulose or crosslinked sodium carboxymethyl starch,
e) 0-10% by weight of hydroxyalkylcellulose, and
f) 0-5% by weight of a conventional lubricant.

Very particularly preferred ibuprofen formulations comprise
a) 50-93.5% by weight of ibuprofen,
b) 1.5-10% by weight of finely divided silica with a surface area of at least 150 m$^2$/g,
c) 5-15% by weight of microcrystalline cellulose,
d) 0-10% by weight of crosslinked polyvinylpyrrolidone, crosslinked sodium carboxymethylcellulose or crosslinked sodium carboxymethyl starch,
e) 0-10% by weight of hydroxyalkylcellulose, and
f) 0-5% by weight of a conventional lubricant.

The process of the invention for producing ibuprofen formulations is carried out in such a way that initially ibuprofen or ibuprofen salt is mixed with the finely divided excipient and optionally further excipients for at least 30 min and then if desired further additives are mixed in. In a preferred embodiment, the ibuprofen is initially mixed with the finely divided excipient.

The process is preferably carried out in such a way that the temperature of the ibuprofen mixing material does not exceed 50° C., preferably 40° C., particularly preferably 35° C., in the respective mixing processes.

The mixing processes can take place in any conventional mixing apparatus. Low-shear mixing tools are preferably employed. Free-fall mixers in which the mixing takes place by agitation of the mixing material in the horizontal or vertical direction are particularly preferably employed. Particularly suitable are Turbula mixers, container mixers or V mixers. The mixers may also comprise mixing aids in fixed or in movable form, leading to a more vigorous mixing process. Fixed mixing aids are internals of widely varying geometry; movable mixing aids mean articles such as, for example, balls or cylinders or similar shaped articles which are put into the mixing material, are mixed with it and thus make the mixing process more vigorous.

The mixing time is at least 0.5 h. It may be from 0.5 h to 8 h, preferably 1 h to 5 h, particularly preferably 1.25 h to 3 h. The mixing time chosen in the individual case depends, besides the type of mixer and its energy input, also on the amount of finely divided excipient employed.

The particles obtained in this way have, as described, a coverage of at least 50% of the surface of the ibuprofen crystals with finely divided excipient.

The surface coverage is assessed visually, preferably with the aid of an image analysis system. This process is based on the analysis of SEM micrographs (SEM: scanning electron microscopy).

In a preferred embodiment of the invention, the ibuprofen crystals covered with finely divided excipient obtained in this way are compacted by roll compaction to agglomerates, and the compacted agglomerates are also referred to hereinafter as compacts. The compacts are then forced through a sieve with a mesh width of from 0.8 to 2.5 mm to result in granules.

The ibuprofen formulations of the invention in the agglomerated form have an average particle size of from 150 µm to 1500 µm, preferably 200 µm to 1200 µm, particularly preferably 250 µm to 1000 µm. Moreover, the fines content, i.e. the proportion of particles with a particle size below 85 µm, is preferably less than 10% by weight.

In a further preferred embodiment of the invention, a further proportion of at least 0.5% by weight and up to 5% by weight, based on the amount of compact, of finely divided excipient is admixed with the granules in a second mixing step. The mixing time can be between 0.3 h and 2 h, and is normally in the region of 1 h. This second mixing step preferably likewise takes place in a free-fall mixer.

Pharmaceutical dosage forms comprising an ibuprofen formulation of the invention can take place in a conventional way by compression of the ibuprofen formulations obtained according to the invention, if appropriate with admixture of further excipients. Suitable further excipients are conventional fillers and binders, disintegrants, lubricants, surface-active substances, flow regulators and masking flavors.

The ibuprofen content of the tablet produced in this way should be at least 60% by weight based on the tablet weight. A higher ibuprofen content may also be advisable for tablets with higher active ingredient dosages in order to keep the tablet weight low.

The active ingredient release from the tablets is at least 80% after 10 min, preferably at least 80% after 5 min, measured by the paddle method at 37° C. in phosphate buffer of pH 7.2 as specified in USP 28 or as specified in Ph. Eur. (European Pharmacopoeia). The disintegration time of the tablets in aqueous medium is less than 2 min.

If desired, the tablets may also be provided with a film coating.

The ibuprofen formulations of the invention exhibit a distinctly improved processing behavior during direct tableting.

EXAMPLES

Example 1

3.5% by weight of finely divided silica[1], 6.77% by weight of microcrystalline cellulose and 3% by weight of croscarmellose sodium were sieved through an 800 µm sieve and introduced into a Turbula mixing container (T10B, 780 mm×955 mm×845 mm). 86.72% by weight of ibuprofen were likewise sieved through an 800 µm sieve and put into the mixer (total mass: 5.0 kg). The mixture was then mixed for 180 min. The coverage of the surface was 85%. The premix obtained in this way was compacted in a compactor (Minipactor 1114, Gerteis) with a compaction force of 6 kN/cm for 3 h. 49% by weight of the compacted material were introduced into a Turbula mixing container (T10B, 780 mm×955 mm×845 mm). 2% by weight of silica were added and then a further 49% by weight of the compact were added (total mass: 5.0 kg=100% by weight). Mixing was then continued for 60 minutes. The coverage of the surface of the agglomerates with finely divided substance was >90%.

[1] Aerosil 200, from Degussa: specific surface area (BET) 200 m$^2$/g

Examples 2 to 4

A mixture of 1% by weight of Aerosil 200 and 99% by weight of ibuprofen 50 (average particle size 50 µm) was mixed in a Turbula mixer for 3 minutes and then sieved through a 1.00 mm sieve.

This mixture was then mixed in the Turbula mixer for various mixing times:
Example 2) 10 minutes
Example 3) 30 minutes
Example 4) 180 minutes The premixes obtained in this way were processed in a Turbula mixer for a period of 10 minutes with the amounts, stated below, of excipients to give a compression mixture:

| Composition of the compression mixture (ibuprofen content: 75% by weight) | Content [% by weight] |
|---|---|
| Premix | 75.76 |
| Microcrystalline cellulose | 20.24 |
| Croscarmellose sodium | 3.0 |
| Aerosil 200 | 0.5 |
| Mg stearate | 0.5 |

These compression mixtures were compressed in a Korsch PH 106 rotary press under a compressive force of 15 kN (30 rpm, punches: 9 mm, shallow curvature, without imprint).

| | |
|---|---|
| Compression mixture with premix of Ex. 2; surface coverage 20% | Adhesion after a compression time of 60 minutes[+)] |
| Compression mixture with premix of Ex. 3; surface coverage 54% | Adhesion after a compression time of 4 hours |
| Compression mixture with premix of Ex. 4; surface coverage > 85% | No adhesion after a compression time of 8 h |

[+)]Running time of the tablet press

We claim:

1. A process for producing a directly tabletable ibuprofen formulation comprising
   a. 50-99% by weight of crystalline ibuprofen;
   b. 1-15% by weight of a finely divided excipient with a surface area of at least 100 $m^2/g$; and
   c. 0-40% by weight of further excipients;
   wherein the total amount of a), b), and c) corresponds to 100% by weight and at least 50% of the surface of the ibuprofen crystals is covered with said finely divided excipient comprising mixing ibuprofen or a salt thereof with finely divided silica for at least 1 hour and then mixing in the remaining additives to form a mixture.

2. The process of claim 1, further comprising roll-compacting said mixture and then forcing the roll-compacted mixture through a sieve to result in granules.

3. The process of claim 2, further comprising admixing at least 0.5% by weight of additional finely divided silica with said granules.

4. A directly tabletable ibuprofen formulation prepared by the process of claim 1.

5. The ibuprofen formulation of claim 4, where the ibuprofen crystals are present in the form of a free acid or as an alkali metal or alkaline earth metal salt or as a salt with a basic amine or amino acid.

6. The ibuprofen formulation of claim 4, where the ibuprofen crystals have an average particle size of from 20 to 200 μm.

7. The ibuprofen formulation of claim 4, wherein at least 60% of the surface of the ibuprofen crystals is covered with said finely divided excipient.

8. The ibuprofen formulation of claim 4, wherein at least 70% of the surface of the ibuprofen crystals is covered with the finely divided excipient.

9. The ibuprofen formulation of claim 4, wherein said finely divided excipient has a surface area of at least 150 $m^2/g$.

10. The ibuprofen formulation of claim 4, wherein said finely divided excipient has a surface area of at least 200 $m^2/g$.

11. The ibuprofen formulation of claim 4, wherein said finely divided excipient has a surface area of at least 250 $m^2/g$.

12. The ibuprofen formulation of claim 4, wherein said finely divided excipient comprises a metal oxide selected from the group consisting of the oxides of aluminum, silicon, zinc, and titanium.

13. The ibuprofen formulation of claim 4, wherein said finely divided excipient comprises silica.

14. The ibuprofen formulation of claim 4, wherein said finely divided excipient comprises hydrophobized silica.

15. The ibuprofen formulation of claim 4, comprising
   a. 50-94% by weight of ibuprofen;
   b. 1-15% by weight of finely divided silica with a surface area of at least 100 $m^2/g$;
   c. 5-20% by weight of microcrystalline cellulose;
   d. 0-10% by weight of crosslinked polyvinylpyrrolidone, crosslinked sodium carboxymethylcellulose, or crosslinked sodium carboxymethyl starch;
   e. 0-10% by weight of hydroxyalkylcellulose; and
   f. 0-5% by weight of a conventional lubricant.

16. The ibuprofen formulation of claim 4, comprising
   a. 50-93.5% by weight of ibuprofen;
   b. 1.5-10% by weight of finely divided silica with a surface area of at least 150 $m^2/g$;
   c. 5-15% by weight of microcrystalline cellulose;
   d. 0-10% by weight of crosslinked polyvinylpyrrolidone, crosslinked sodium carboxymethylcellulose, or crosslinked sodium carboxymethyl starch;
   e. 0-10% by weight of hydroxyalkylcellulose; and
   f. 0-5% by weight of a conventional lubricant.

17. The ibuprofen formulation of claim 4, wherein said further excipients are selected from the group consisting of fillers, binders, disintegrants, lubricants, and mixtures thereof.

18. The ibuprofen formulation of claim 4, further comprising fillers selected from the group consisting of microcrystalline cellulose, cellulose, calcium hydrogen phosphate, mannitol, sorbitol, xylitol, and lactose.

19. The ibuprofen formulation of claim 4, further comprising binders selected from the group consisting of polyvinylpyrrolidone, vinylpyrrolidone/vinyl acetate copolymers, hydroxypropylmethylcellulose, hydroxypropylcellulose, hydroxyethylcellulose, and methylcellulose.

20. The ibuprofen formulation of claim 4, further comprising disintegrants selected from the group consisting of crosslinked sodium carboxymethyl starch, crosslinked sodium carboxymethylcellulose, and crosslinked polyvinylpyrrolidone.

21. The ibuprofen formulation of claim 4, further comprising disintegrants selected from the group consisting of stearic acid, magnesium stearate, sodium stearyl fumarate, leucine, sodium benzoate, and poloxamers.

22. The ibuprofen formulation of claim 4, wherein the ibuprofen crystals covered with said finely divided excipient are agglomerates, wherein the average particle size of said agglomerates are in the range of from 150 to 1500 μm.

23. The ibuprofen formulation of claim 22, wherein the average particle size of said agglomerates are in the range of from 200 and 1200 μm.

24. The ibuprofen formulation of claim 22, wherein the average particle size of said agglomerates are in the range of from 250 and 1000 μm.

25. The ibuprofen formulation of claim 22, wherein the average particle size of said agglomerates are in the range of from 250 and 1000 μm and the proportion of agglomerates having particle sizes of less than 85 μm is less than 10% by weight.

26. The ibuprofen formulation of claim 4, wherein the average particle size of said agglomerates are in the range of from 250 and 1000 μm and the proportion of agglomerates having particle sizes of less than 85 μm is less than 6% by weight.

27. The ibuprofen formulation of claim 4, wherein the ibuprofen crystals covered with said finely divided excipient are agglomerates, wherein the surface of said agglomerates is at least 50% covered with said finely divided excipient.

28. A process for producing the ibuprofen formulation of claim 4 comprising mixing ibuprofen particles with a finely divided excipient which has a surface area of at least 100 $m^2/g$ until at least 50% of the surface of the ibuprofen particles is covered with said finely divided excipient, wherein said mixing time is at least one hour.

29. The process of claim 28, wherein the temperature of said ibuprofen during the mixing process exceeds 50° C.

30. A pharmaceutical dosage form comprising the ibuprofen formulation of claim 4, wherein said pharmaceutical dosage form is produced by compression.

31. The pharmaceutical dosage form of claim 30, where the ibuprofen content of said pharmaceutical dosage form is at least 60% by weight.

* * * * *